(12) United States Patent
Kanai et al.

(10) Patent No.: US 10,458,924 B2
(45) Date of Patent: Oct. 29, 2019

(54) INSPECTION APPARATUS AND INSPECTION METHOD

(71) Applicant: HITACHI HIGH-TECHNOLOGIES CORPORATION, Tokyo (JP)

(72) Inventors: Hisaaki Kanai, Tokyo (JP); Masami Makuuchi, Tokyo (JP); Yukihisa Mohara, Tokyo (JP); Eiji Imai, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 16/311,103

(22) PCT Filed: Jul. 4, 2016

(86) PCT No.: PCT/JP2016/069731
§ 371 (c)(1),
(2) Date: Dec. 18, 2018

(87) PCT Pub. No.: WO2018/008051
PCT Pub. Date: Jan. 11, 2018

(65) Prior Publication Data
US 2019/0178813 A1     Jun. 13, 2019

(51) Int. Cl.
*G01N 21/88* (2006.01)
*G01N 21/95* (2006.01)
*G01N 21/956* (2006.01)

(52) U.S. Cl.
CPC ....... *G01N 21/9501* (2013.01); *G01N 21/956* (2013.01)

(58) Field of Classification Search
CPC ........ G06T 5/00; G06K 9/52; G06K 9/00281; G01N 21/9501; G01N 21/956;
(Continued)

(56) References Cited

U.S. PATENT DOCUMENTS 5,422,964 A * 6/1995 Devimeux ........... H04N 19/527
                                                                 358/461
6,621,571 B1    9/2003 Maeda et al.
(Continued)

FOREIGN PATENT DOCUMENTS

JP    53-134484 A    11/1978
JP    60-245240 A    12/1985
(Continued)

OTHER PUBLICATIONS

International Search Report for PCT/JP2016/069731, dated Sep. 27, 2016.

*Primary Examiner* — Hoa Q Pham
(74) *Attorney, Agent, or Firm* — Volpe and Koenig, P.C.

(57) ABSTRACT

A defect inspection apparatus includes a light irradiation unit irradiating a sample placed on a table unit with illumination light, a detection optical system forming a scattered light image from the sample and detecting the generated scattered light image through an image sensor, a processing unit receiving a signal from the image sensor of the detection optical system that detects the scattered light image, generating an image of the scattered light, and detecting a defect of the sample by processing the generated image, an output unit outputting the defect image processed by the image processing unit, and a control unit controlling the stable unit, the light irradiation unit, the detection optical system, and the image processing unit. The image processing unit includes an image generation unit that receives the signal and generates the image, a correction unit that corrects lightness discontinuity and a defect detection unit for image processing.

8 Claims, 8 Drawing Sheets

(58) Field of Classification Search
CPC . G01N 2021/8887; G01N 2021/95615; G01N 2021/95607; H04N 1/6027
USPC ......... 356/237.1–237.5; 382/226, 232, 149; 358/461, 463, 2.1, 3.23, 530
See application file for complete search history.

(56) References Cited

U.S. PATENT DOCUMENTS

| | | | | |
|---|---|---|---|---|
| 7,706,022 | B2* | 4/2010 | Okuyama | H04N 1/6027 358/2.1 |
| 8,947,588 | B2* | 2/2015 | Shirakawa | H04N 5/2354 348/371 |
| 2012/0294507 | A1* | 11/2012 | Sakai | G01N 21/956 382/149 |
| 2013/0242294 | A1* | 9/2013 | Taniguchi | G01N 21/956 356/237.5 |
| 2015/0369752 | A1* | 12/2015 | Honda | G01N 21/8851 356/237.2 |

FOREIGN PATENT DOCUMENTS

| | | | |
|---|---|---|---|
| JP | 64-24564 | A | 1/1989 |
| JP | 2001-194323 | A | 7/2001 |
| JP | 2002-310934 | A | 10/2002 |
| JP | 2006-84189 | A | 3/2006 |
| JP | 2012-181135 | A | 9/2012 |
| JP | 2016-023999 | A | 2/2016 |

* cited by examiner

[FIG. 1]
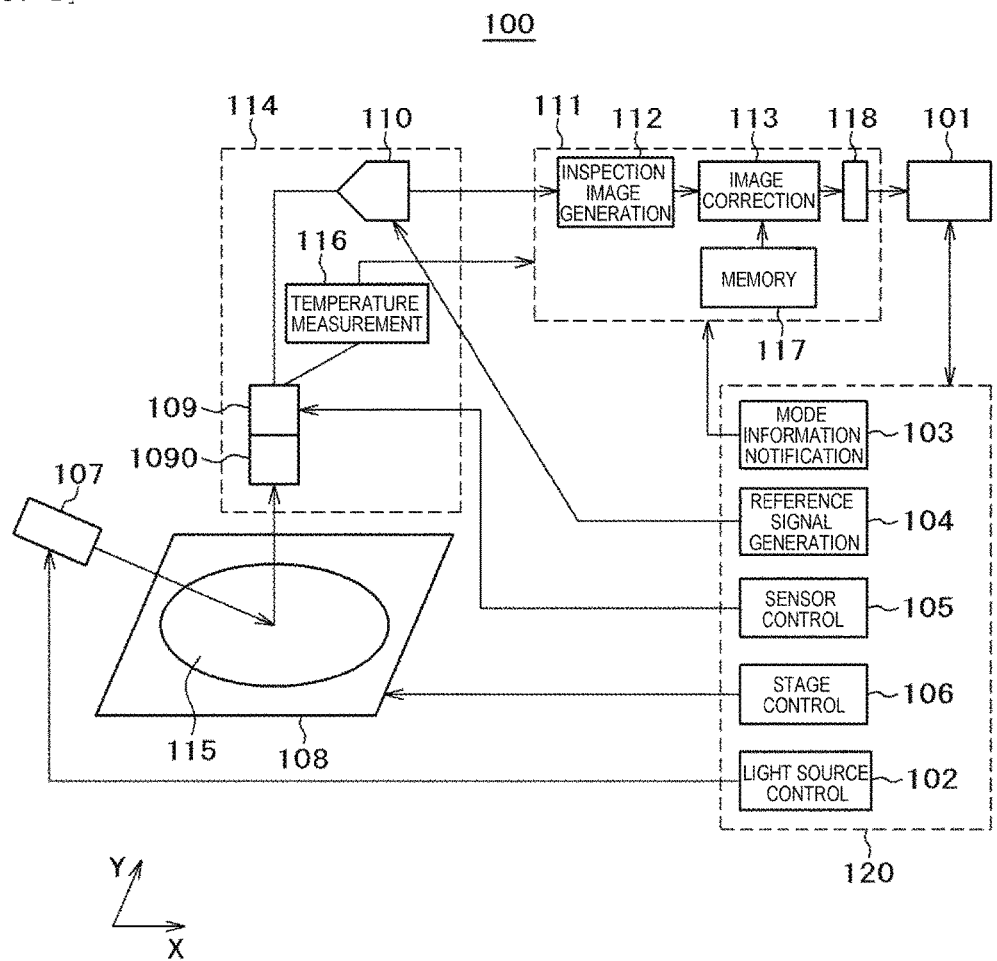
[FIG. 2A]
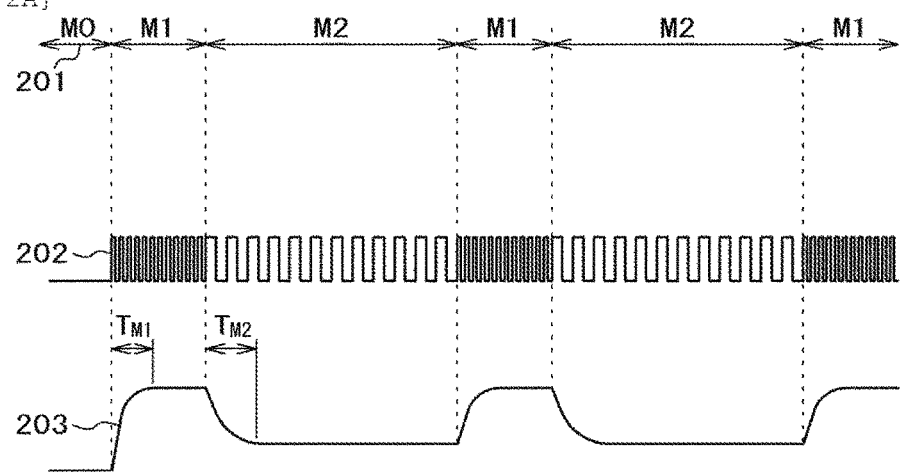

[FIG. 2B]
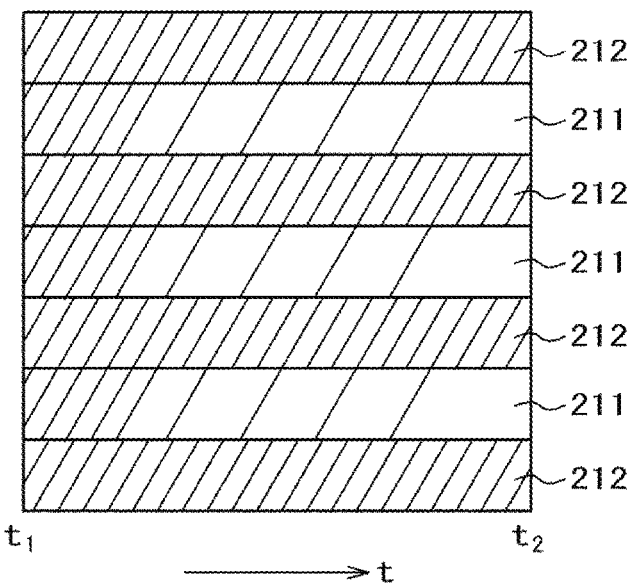
[FIG. 3]

[FIG. 4]
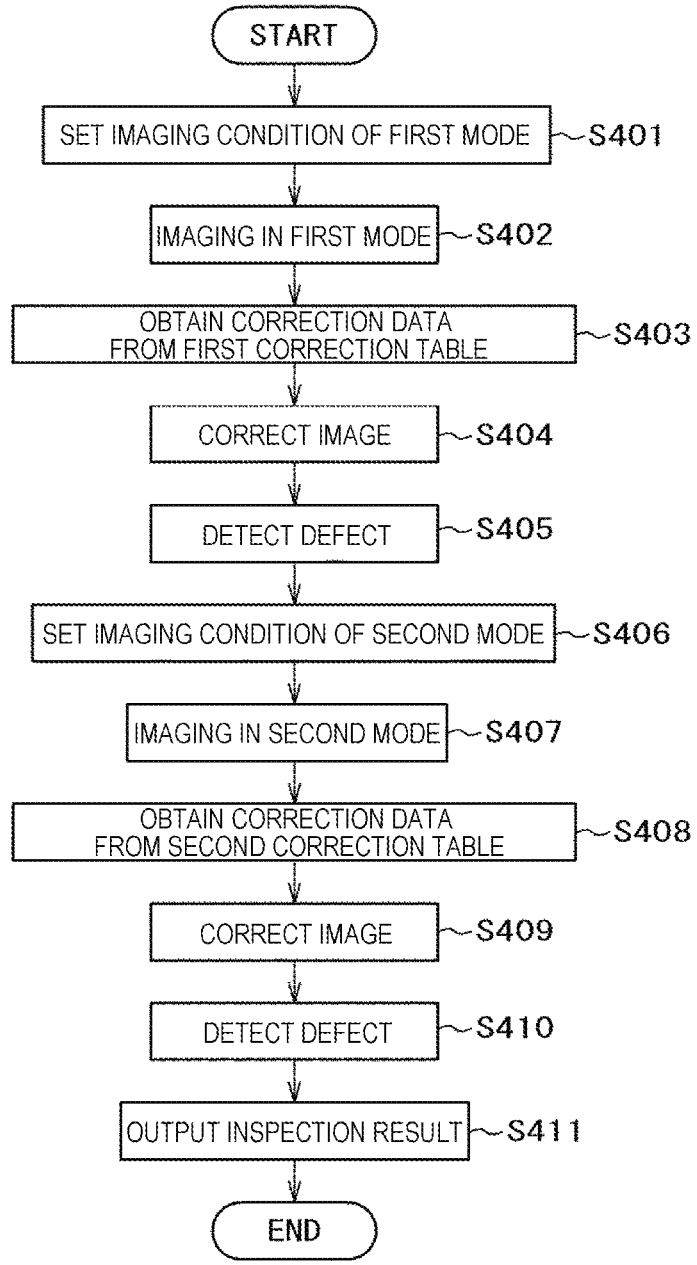

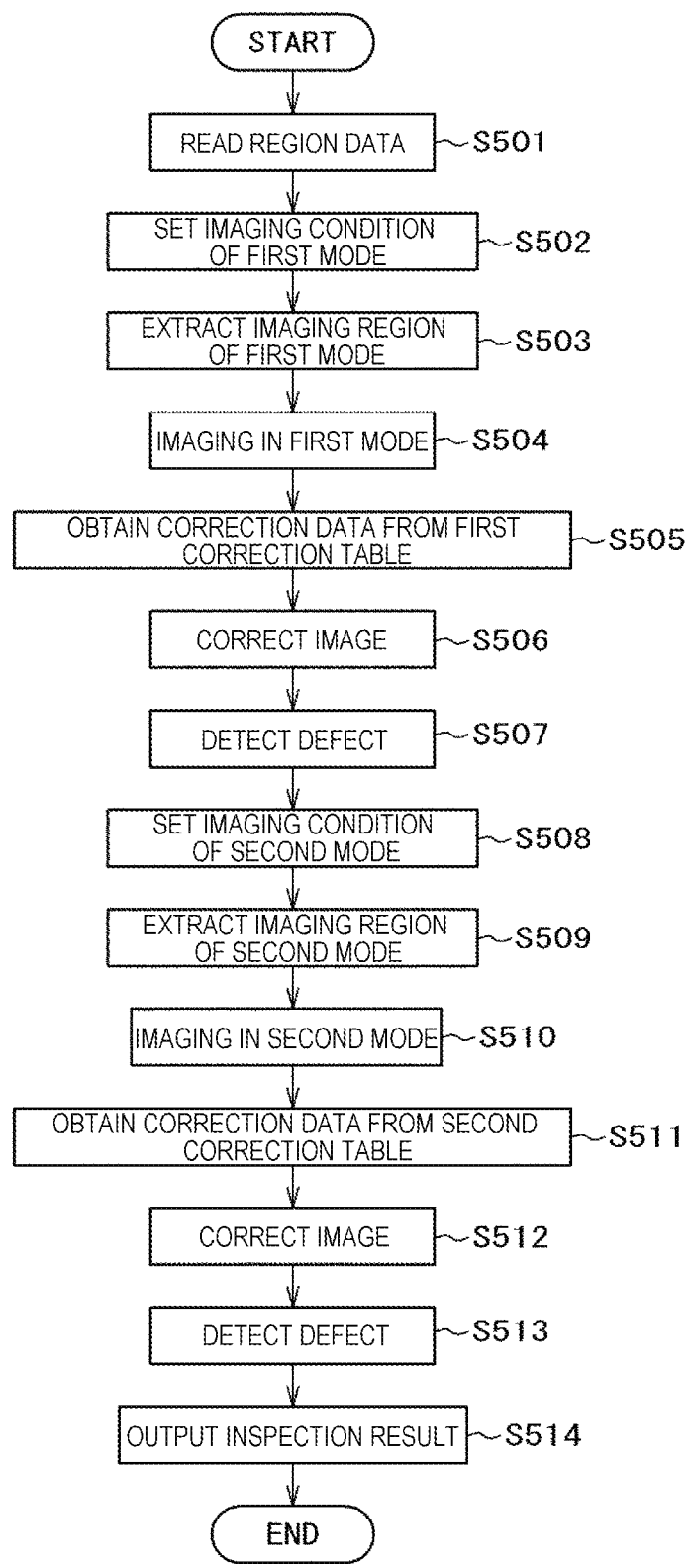
[FIG. 5]

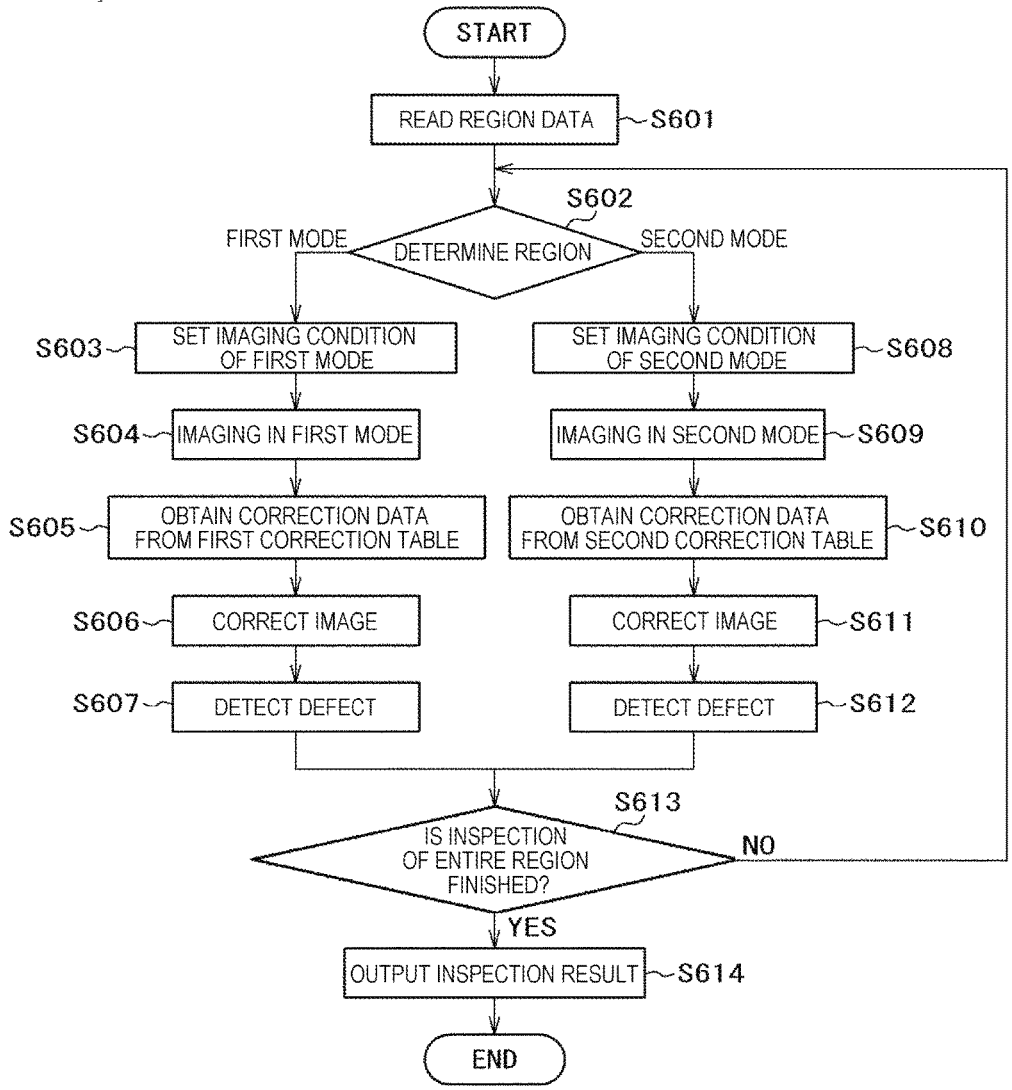

[FIG. 7]
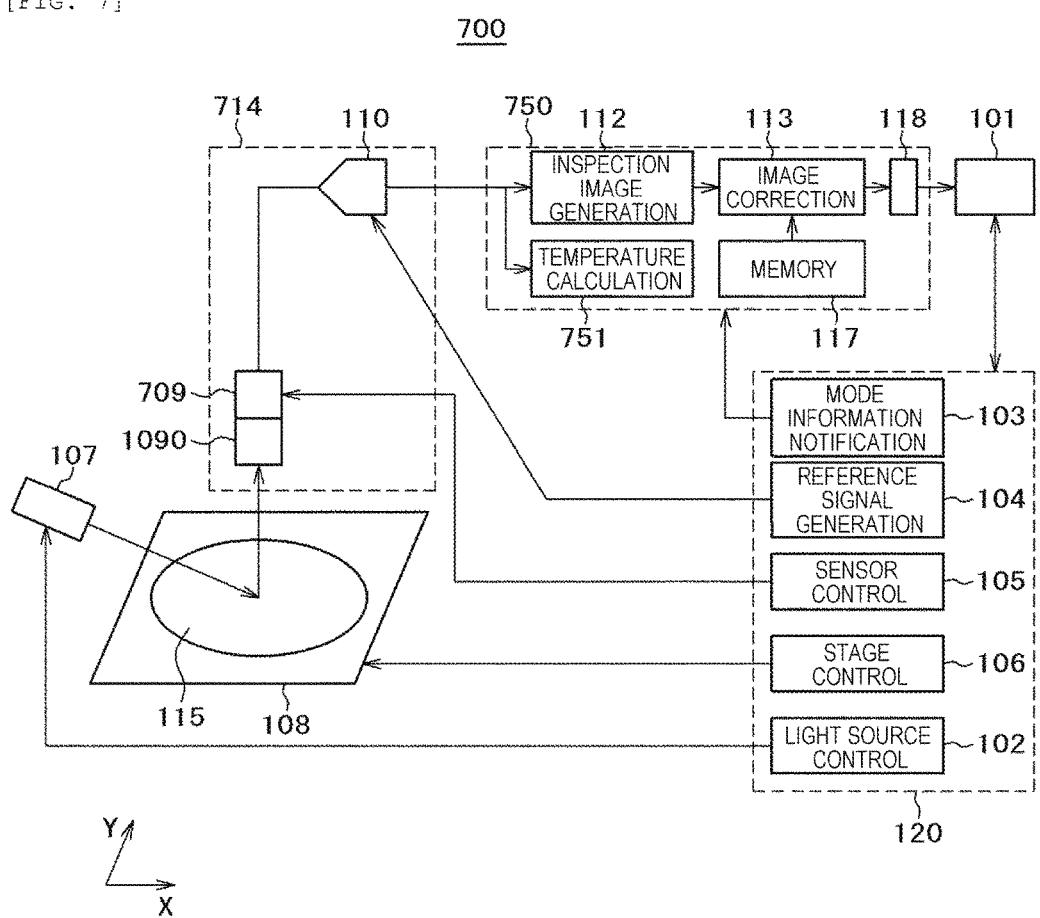
[FIG. 8]
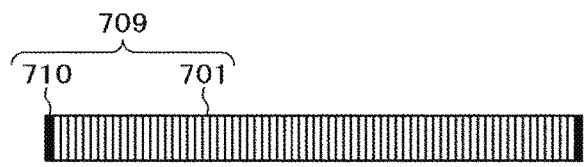

[FIG. 9]
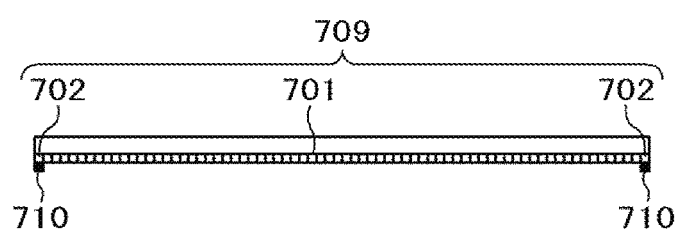
[FIG. 10]
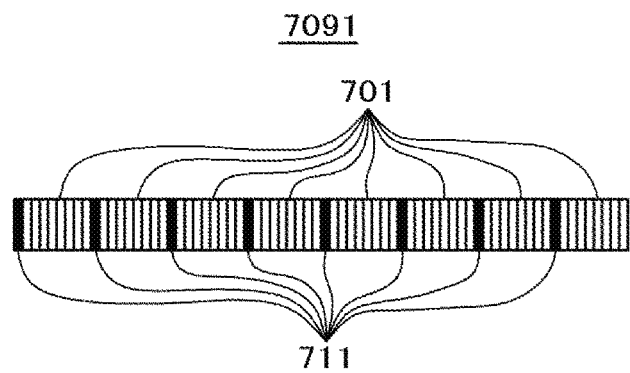

[FIG. 11]
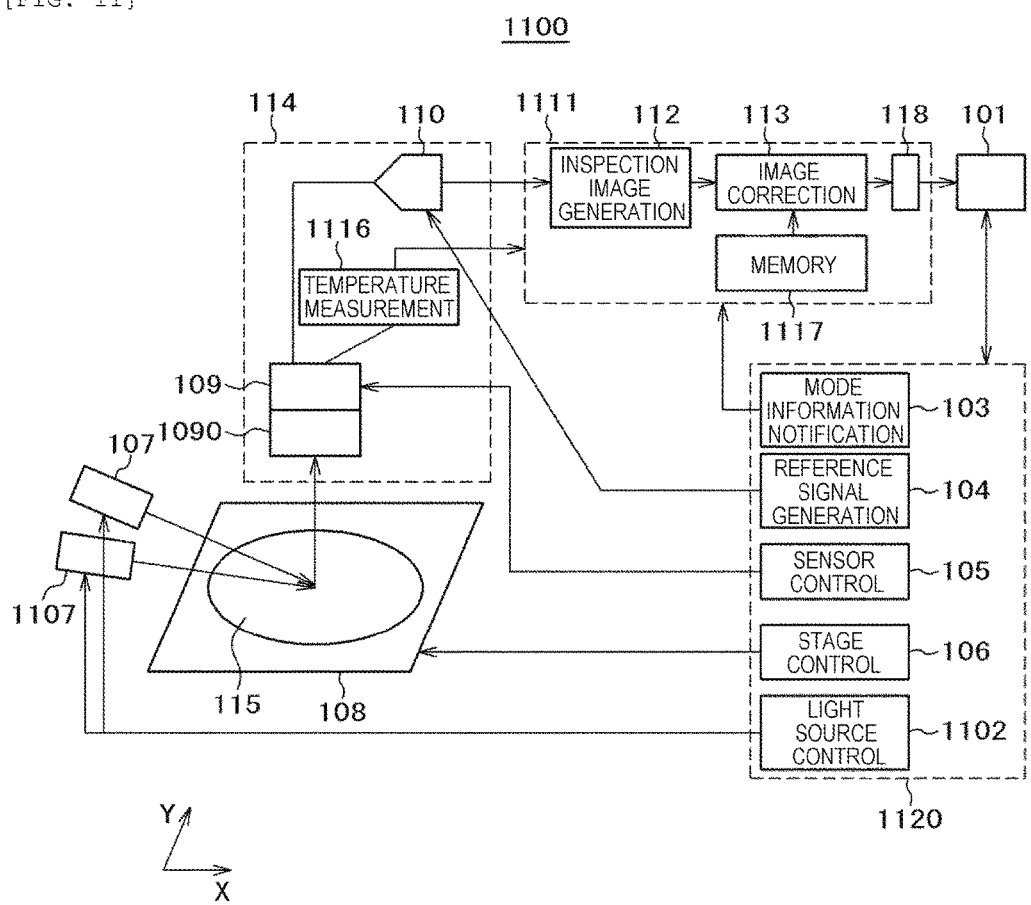

INSPECTION APPARATUS AND INSPECTION METHOD

TECHNICAL FIELD

The present invention relates to an inspection apparatus and an inspection method for inspecting, measuring, or observing defects in a semiconductor wafer, semiconductor equipment (semiconductor integrated circuit device), a photomask (exposure mask), a liquid crystal panel, etc.

BACKGROUND ART

As a semiconductor inspection device related to the present invention, there is disclosed in JP-A-2016-023999 (PTL 1). The above publication discloses that "a semiconductor inspection apparatus for inspecting a semiconductor wafer by receiving scattered light generated by irradiating a wafer to be inspected with light with a plurality of detectors, the semiconductor inspection apparatus includes a control unit for controlling the semiconductor inspection apparatus and outputting an inspection speed signal relating to an inspection speed, a signal calculation unit that calculates a detector control signal for controlling the operation of the detector based on the inspection speed signal output from the control unit, and a signal generation unit for generating a signal synchronized with the control signal of the first detector and the control signal of the second detector."

CITATION LIST

Patent Literature

PTL 1: JP-A-2016-023999

SUMMARY OF INVENTION

Technical Problem

An optical inspection device measures a wafer pattern shape and inspects defects by irradiating a wafer with a laser beam and detecting scattered light from the wafer. Recently, miniaturization of semiconductor processes and complication such as a three-dimensional shape have progressed, patterns or defects formed on a wafer are more complicated and have smaller sizes than those of the prior art. Accordingly, scattered light from the wafer is becoming weak and a detection signal obtained from an image sensor (e.g., a CCD sensor and a CMOS sensor) that detects the scattered light also decreases in proportion to an intensity of scattered light and thus, a detection method of high sensitivity is required. On the other hand, in order to reduce manufacturing costs, an inspection method of a high throughput is required. That is, in such an inspection apparatus, both of high sensitivity and high throughput have been required recently.

In order to solve the above problems, PTL 1 discloses a method of adjusting an internal operating speed in response to a request by making the internal operating speed of a detection system variable. According to PTL 1, when a highly sensitive detection is required, the internal operating speed is decreased to increase an accumulated charge amount of the image sensor in order to improve a signal-to-noise ratio (SN ratio), and when a high-throughput inspection is required, an internal operating speed of a detection system may be increased to improve the throughput.

Meanwhile, when an internal operating speed of the detection system is changed, a temperature around the image sensor or a peripheral circuit excessively changes, lightness discontinuity occurs in a detection image immediately after switching the internal operating speed. Therefore, after switching a mode, an idling period is necessary to stabilize the temperature, and thus there is an issue that the throughput decreases.

The present invention has been made to solve the above problems of the prior art, and an object thereof is to provide an inspection apparatus and an inspection method capable of preventing a throughput from degrading due to an idling period when an internal operating speed of a detection system is changed.

Solution to Problem

The typical ones of the inventions disclosed in the present application will be briefly described as follows.

That is, in order to address the above problems of the prior art, the present invention provides an inspection apparatus including a table unit that is movable with a sample placed thereon, a light irradiation unit irradiating the sample placed on the table unit with illumination light, a detection optical system forming a scattered light image from the sample and detecting the generated scattered light image through an image sensor, an image processing unit receiving a signal from the image sensor of the detection optical system that detects the scattered light image, generating an image of the scattered light, and detecting a defect of the sample by processing the generated image, an output unit outputting the image including the defect processed by the image processing unit, and a control unit controlling the table unit, the light irradiation unit, the detection optical system, and the image processing unit, wherein the image processing unit includes an image generation unit receiving the signal from the image sensor and generating the image of the scattered light, an image correction unit correcting lightness discontinuity that occurs in the image of the scattered light, the image being generated by the image generation unit, and a defect detection unit processing the image, on which the lightness discontinuity is corrected by the image correction unit, to detect a defect of the sample.

In order to solve the above problems of the prior art, the present invention provides an inspection method including irradiating a sample placed on a table unit with illumination light from a light irradiation unit, generating a scattered light image by condensing the scattered light from the sample irradiated with the illumination light, in a detection optical system and detecting the generated scattered light image by using an image sensor, Generating an image of the scattered light by receiving a signal from the image sensor that detects the scattered light image in an image processing unit and processing the generated image to detect a defect of the sample, outputting, by an output unit, an image including the defect processed by the image processing unit, and controlling, by a control unit, the table unit, the light irradiation unit, the detection optical system, and the image processing unit, wherein the detecting of the defect of the sample by the image processing unit includes generating, by an image generation unit, an image of the scattered light after receiving a signal from the image sensor, correcting, by an image correction unit, a lightness discontinuity that occurs in the image of the scattered light, the image being generated by the image generation unit, and detecting, by a defect detection unit, a defect in the sample by processing the image, the lightness discontinuity of which is corrected by the image correction unit.

Advantageous Effects of Invention

Effects obtained by the typical ones of the inventions disclosed in the present application will be briefly described as follows.

According to a typical embodiment of the present invention, even when an internal operating speed is changed, an idling period until a temperature is stabilized is not necessary, and an inspection throughput may be improved.

BRIEF DESCRIPTION OF DRAWINGS

FIG. 1 is a block diagram schematically illustrating an inspection apparatus according to a first embodiment of the present invention.

FIG. 2A is a diagram illustrating an image sensor control signal and a variation in a temperature of the image sensor according to time when an inspection mode of the inspection apparatus according to the first embodiment of the present invention is changed.

FIG. 2B is a diagram illustrating an example of a line pattern image captured when an inspection mode of the inspection apparatus according to the first embodiment of the present invention is changed from a high sensitivity mode to a high throughput mode.

FIG. 3 is a diagram illustrating an example of a correction table held by a memory according to the first embodiment of the present invention.

FIG. 4 is a flowchart illustrating processes of correcting an image and detecting a defect according to the first embodiment of the present invention.

FIG. 5 is a flowchart illustrating a first modified example of processes of correcting an image and detecting a defect according to the first embodiment of the present invention.

FIG. 6 is a flowchart illustrating a second modified example of processes of correcting an image and detecting a defect according to the first embodiment of the present invention.

FIG. 7 is a block diagram schematically illustrating an inspection apparatus according to a second embodiment of the present invention.

FIG. 8 is a front view of an image sensor in the inspection apparatus according to the second embodiment of the present invention.

FIG. 9 is a plan view of an image sensor in the inspection apparatus according to the second embodiment of the present invention.

FIG. 10 is a front view illustrating another configuration of the image sensor in the inspection apparatus according to the second embodiment of the present invention.

FIG. 11 is a block diagram schematically illustrating an inspection apparatus according to a third embodiment of the present invention.

DESCRIPTION OF EMBODIMENTS

According to the present invention, in an inspection apparatus, a detected image is corrected after selecting a correction coefficient stored in a memory based on an operating speed of a detection unit, a temperature of an image sensor, and pixels.

That is, according to the present invention, in order to address a problem that a throughput is reduced because an idling period is necessary until a temperature is stabilized immediately after switching an inspection mode in an inspection apparatus that may switch an operating speed of a detection system, in an image processing system constituting the inspection apparatus, a memory storing a correction coefficient of an image sensor for each image sensor temperature, each image sensor pixel, and each inspection mode is provided, and an image correction unit that corrects an image by using the image obtained by an inspection image obtaining unit and a correction coefficient according to a temperature sensor and an inspection mode is configured so that an idling period is not necessary even when the inspection mode of the detection system is changed and an inspection throughput may be increased.

Hereinafter, one or more embodiments of the present invention will be described below with reference to accompanying drawings. Also, components having the same function are denoted by the same reference numerals throughout the drawings for describing the embodiment, and the repetitive description thereof is omitted. Also, the basic operation of the inspection apparatus in each embodiment, is omitted because it is similar to the inspection apparatus according to the prior art, and operations and gist related with each embodiment will be only described.

First Embodiment

FIG. 1 is a diagram illustrating a configuration of an inspection apparatus 100 according to a first embodiment. The inspection apparatus 100 according to the first embodiment includes a stage 108 that is movable with a wafer 115 that is to be inspected loaded thereon, a light source 107 for irradiating the wafer 115 loaded on the stage 108 with light, a detection system 114 including an imaging optical system 1090 for converging scattered light from the wafer 115, irradiated with the light from the light source 107, and forming a scattered light image, an image sensor 109 for detecting the image formed by the imaging optical system 1090, an ADC 110 for converting a signal obtained from the image sensor 109 to a digital signal, and a temperature measurement unit 116 for measuring a temperature of the image sensor 109, an image processing system 111 for generating an inspection image of the wafer pattern to perform an image correction and generating a correction detected image to inspect a wafer pattern by receiving an output signal from the detection system 114, a display system 101 for displaying an image with a defect of the wafer pattern detected by the image processing system 111, and a device control system 120 for controlling the detection system 114, the image processing system 111, the display system 101, and the stage system 115.

The device control system 120 includes a mode information notification unit 103 for notifying the image processing system 111 of a detection mode that set through the display system 101, a reference signal generation unit 104 for outputting a reference signal according to the detection mode to the ADC 110, a sensor control unit 105 for outputting a control signal according to the detection mode to the image sensor 109, a stage control unit 106 for manipulating the stage 108, and a light source control unit 102 for controlling power of the light source 107.

The image processing system 111 includes an image generation unit 112 for generating an inspection image from a detection signal of the detection system 114, a memory 117 for retaining a correction coefficient for each of the temperature of the image sensor 109, the inspection mode, and each location of the pixel, an image correction unit 113 that corrects a detection image generated by the image generation unit 112 by using the correction coefficient selected according to the temperature of the image sensor 109, the inspection mode, and pixel location information, and a defect detection unit 118 for detecting a defect in a pattern formed on the wafer 115 to be inspected by processing the image corrected by the image correction unit.

In the above configuration, an operator of the inspection apparatus 100 may set or select an inspection condition, etc. from a graphical user interface (GUI) displayed on a display screen of the display system 101 or a user interface (not illustrated, e.g., a manipulation panel, a keyboard, reading of a description file (also referred to as a recipe) including inspection information, condition, etc.), connected to the device control system 120.

In the above configuration, the light source control unit 102 controls an electric power of the light source 107 according to the set or selected inspection condition (hereinafter, referred to as setting) to irradiate the wafer 115 loaded on the stage 108 with light According to the set inspection condition in this state, the stage control unit 106 controls the stage 108 to move continuously in a direction at a predetermined speed, and the scattered light image from the wafer 115 is detected by the image sensor 109 that is controlled based on the inspection condition set by the sensor control unit 105 via the imaging optical system 1090.

An output signal from the image sensor 109 that detects the scattered light image from the wafer 115 is converted into a digital signal in the ADC 110 and input to the image processing system 111, and an inspection image of the wafer pattern is generated by the inspection image generation unit 112. The generated inspection image is corrected in the image correction unit 113 by using the correction coefficient that is stored and corrected in the memory 117, and then is compared with a reference image in the defect detection unit 118 to detect a defect in the pattern formed on the wafer 115.

Here, in a case where the inspection is performed while switching between a high sensitivity mode, in which a moving velocity of the stage 108 is relatively slower to inspect a relatively narrow region of the wafer 115 with high sensitivity, and a high throughput mode, in which the moving velocity of the stage 108 is relatively faster to inspect a relatively wide region at a relatively high speed, the inspection is performed based on the inspection condition set according to each mode while the device control system 120 controls each component of the inspection apparatus 100.

FIG. 2A is a diagram illustrating a variation in a sensor control signal and a sensor temperature according to time when switching the inspection mode between the high throughput mode and the high sensitivity mode. As a unit for measuring the sensor temperature, a thermocouple thermometer, an infrared ray thermometer, etc. may be used. In FIG. 2A, 201 denotes a mode state (detection mode) at each time point, 202 denotes a sensor control signal applied by the sensor control unit 105 to the image sensor 109, and 203 denotes a variation in the sensor temperature according to time.

When the detection mode 201 starts to operate in a high throughput mode (M1) from an inspection suspended state (M0), the sensor control signal 202 is output to the image sensor 109. In the image sensor 109 and a peripheral circuit (not illustrated) of the image sensor 109, electric power is consumed according to an input of the sensor control signal of the sensor control unit 105, the sensor temperature 203 rises, and the temperature is stabilized according to elapse of time.

Next, when the detection mode 201 is switched from the high throughput mode M1 to a high sensitivity mode M2, the sensor control signal 202 has a lower speed as compared with that of the high throughput mode Ml, and since the power consumption in the image sensor 109 and the peripheral circuit (not illustrated) decrease, the sensor temperature 203 is lowered as compared with that of the high throughput mode M1.

Since the sensitivity of the image sensor 109 depends upon the temperature, even when light of the same light intensity is received, a level of a signal output from the image sensor 109 having higher temperature is greater than that of the image sensor 109 having lower temperature (sensitivity is greater). Therefore, in the case in which the temperature of the image sensor 109 varies while the image sensor 109 detects the scattered light from the wafer 115, the signal output from the image sensor 109 varies even when the light of the constant light intensity is continuously received, and accordingly, lightness discontinuity occurs in the obtained image.

As illustrated with reference to FIG. 2A, immediately after switching the detection mode 201, the sensor temperature 203 changes due to the switching of the electric power applied from the sensor control unit 105 to the sensor 109. Accordingly, the lightness discontinuity also occurs in the detected image.

FIG. 2B illustrates an example of a temporal variation in a contrast of an image 210 of a line pattern that is detected by the image sensor 109 and generated on the wafer 115 by the inspection image generation unit 112 immediately after switching the high sensitivity mode M2 to the high throughput mode M1 in FIG. 2A.

FIG. 2B illustrates a state in which the time elapses from ti to t2, from a left side to a right side of FIG. 2B. A reference numeral 211 denotes a convex portion of a lane pattern, and a reference numeral 212 denotes a concave portion of the line pattern. Immediately after switching from the high sensitivity mode M2 to the high throughput mode M1 (time t1), as illustrated in the sensor temperature 203 of FIG. 2A, the sensitivity degrades because the temperature of the image sensor 109 may not reach a normal state of the high throughput mode Ml, a contrast of the detected image (a ratio between brightness of the convex portion 211 and the concave portion 212) decreases and it is difficult to distinguish the convex portion 211 from the concave portion 212.

Regarding to this, at the right side of FIG. 2B (time t2) where a predetermined time has elapsed since the high sensitivity mode M2 is switched to the high throughput mode Ml, the contrast of the detected image is increased and it may be easy to distinguish the convex portion 211 from the concave portion 212.

As described above, when the defect detection unit 118 performs a defect detection process by using the image in which the lightness discontinuity occurs, there is a possibility of erroneously detecting a false alarm, which is generated due to the lightness discontinuity of image that is actually with no defect, as a defect.

As a method of preventing the above erroneous detection, the inspection may be suspended until the temperature of the image sensor 109 is stabilized (time TM1 and time TM2 represented in the sensor temperature 203 of FIG. 2A) immediately after switching the detection mode, and then the inspection restarts after stabilizing the temperature of the image sensor 109. However, according to the above method, the throughput is decreased during suspending of the inspection.

On the other hand, according to the present embodiment, the lightness discontinuity that occurs on the detected image is corrected by the image correction unit 113 of the image processing system 111, and the defect detection unit 118 may accurately detect the defect by using the image on which the lightness discontinuity is corrected, to thereby cancel the inspection suspension time and improve the inspection throughput.

In detail, in the image processing system 111, a correction coefficient is selected from a correction coefficient table retained in the memory 117 according to sensor temperature information of the image sensor 109 detected by the temperature measurement unit 116 attached to the image sensor 109 and detection mode information output from the mode information notification unit 103 of the device control system 120. The image correction unit 113 performs an image processing such as an offset processing, a gain correction, etc. on the inspection image generated by the inspection image generation unit 112 by using the correction coefficient selected as above, and thus, the lightness discontinuity of the image that occurs during changing of the temperature of the image sensor 109 immediately after the mode switching may be corrected.

FIG. 3 illustrates an example of a correction coefficient table 300 retained in the memory. In the correction coefficient table 300, data for each sensor temperature and each sensor pixel is prepared for each inspection mode (in the example of FIG. 3, a correction coefficient table 301 corresponding to an inspection mode 1 and a correction coefficient table 302 corresponding to an inspection mode 2). In order to reduce an amount of retained data, the correction coefficient table 300 according to the present embodiment prepares data with respect to, for example, each discrete temperature. In this case, when the sensor temperature is between the prepared correction coefficient tables, the inspection image maybe corrected by supplementation from the correction coefficients of the correction coefficient tables of previous and next sensor temperatures.

The sensor temperature may be measured by various methods, for example, a thermocouple measurement, an infrared ray measurement, etc.

A flow of processes of correcting an obtained inspection image while inspecting a wafer according to the present embodiment will be described below with reference to FIG. 4. The flow of processes illustrated in FIG. 4 is about a case, in which a region in the wafer 115 to be imaged is imaged by the image sensor 109 and inspected while the stage control unit 106 moves the stage 108 continuously in a direction (X direction) in the inspection mode 1 (high throughput mode) and after that a designated region of the wafer 115 is inspected in the inspection mode 2 (high sensitivity mode).

To begin with, the device control system 120 controls each component in the inspection apparatus 100 to be set in a condition of a first inspection mode (S401), and in this state, the image sensor 109 captures an image of the wafer 115 and the inspection image generation unit 112 generates an inspection image (S402).

Next, the image processing system 111 obtains correction data from a first correction table corresponding to the first inspection mode retained in the memory 117, based on temperature information of the image sensor 109 detected by the temperature measurement unit 116 (S403).

Next, the inspection image generated by the inspection image generation unit 112 is corrected by using the obtained correction data (S404).

Next, the corrected inspection image is sent to the defect detection unit 118 and compared with a reference image to detect a defect (S405). The reference image may be generated by using the corrected inspection image or by using design data.

Next, the inspection image corrected in step S404 is displayed on the display system 101, and with respect to a region designated by an operator, the device control system. 120 controls each component of the inspection apparatus 100 to be set in a condition of a second inspection mode (S406), and in this state, the image sensor 109 captures an image of the wafer 115 and the inspection image generation unit 112 generates an inspection image (S407).

Next, the image processing system 111 obtains correction data from a second correction table corresponding to the inspection mode 2 stored in the memory 117, according to temperature information of the image sensor 109 detected by the temperature measurement unit 116 (S408).

Next, the inspection image generated by the inspection image generation unit 112 is corrected by the obtained correction data (S409).

The corrected inspection image is sent to the defect detection unit 118 and compared with a reference image to detect a defect (S410). The reference image may be generated by using the corrected inspection image or by using design data.

Finally, an inspection result is output from the defect detection unit 118 to the display system 101 (S411), and the inspection process is finished.

According to the present embodiment, since the defect is detected from the image captured by the image sensor 109 after correcting the image based on temperature measurement data of the image sensor 109 at the time of imaging, the inspection may be definitely performed on the image data obtained immediately after switching the inspection mode. As a result, immediately after switching the inspection mode, the inspection image may be generated without waiting for the stabilization of the temperature of the image sensor 109, and thus the inspection throughput may be improved in a case where the inspection is performed while switching the inspection mode.

[MODIFIED EXAMPLE 1]

FIG. 5 illustrates a modified example of the processing flow illustrated in above first embodiment. According to the present modified example, pattern information of an inspection area is obtained and a region to be inspected in a first inspection mode and a region to be inspected in a second inspection mode are discriminated in advance, the region to be inspected in the first inspection mode is totally inspected by using location information of the wafer 115 while the stage control unit 106 moves the stage 108 continuously in one direction (X direction), and then, the region to be inspected in the second inspection mode is totally inspected by using the location information of the wafer 115 while the stage control unit 106 moves the stage 108 continuously in one direction (X direction).

In the present modified example, the pattern information of the inspection area is obtained first, and then, the region to be inspected in the first inspection mode and the region to be inspected in the second inspection mode are discriminated (S501).

Next, the device control system 120 controls each component of the inspection apparatus 100 to be set in a condition of the first inspection mode (S502), and the region to be inspected in the first inspection mode is extracted by using the location information of the wafer 115 while the stage control unit 106 moves the stage 108 continuously in one direction (X direction) (S503).

Next, the extracted region is imaged by the image sensor 109 and the inspection image generation unit 112 generates an inspection image (S504).

Next, the image processing system 111 acquires correction data from a first correction table corresponding to the first inspection mode in the correction table 300 retained in the memory 111 based on temperature information of the image sensor 109 detected by the temperature measurement unit 116 (S505).

Next, the inspection image generated by the inspection image generation unit 112 is corrected by using the obtained correction data (S506).

The corrected inspection image is sent to the defect detection unit 118 and compared with a reference image to detect a defect (S507). The reference image may be generated by using the corrected inspection image or by using design data.

Processes from S504 to S507 are repeatedly performed on an image obtained from the inspection area under the condition of the first inspection mode.

Next, the device control system 120 controls each component of the inspection apparatus 100 to be set in a condition of the second inspection mode (S508), and the region to be inspected in the second inspection mode is extracted by using the location information of the wafer 115 while the stage control unit 106 moves the stage 108 continuously in one direction (X direction) (S509).

Next, the extracted region is imaged by the image sensor 109 and the inspection image generation unit 112 generates an inspection image (S510).

Next, the image processing system 111 obtains correction data from a second correction table corresponding to the second inspection mode retained in the memory 117, based on temperature information of the image sensor 109 detected by the temperature measurement unit 116 (S511).

Next, the inspection image generated by the inspection image generation unit 112 is corrected by using the correction data obtained from the second correction table (S512).

The corrected inspection image is sent to the defect detection unit 118 and compared with a reference image to detect a defect (S513). The reference image may be generated by using the corrected inspection image or by using design data.

Processes from S509 to S512 are repeatedly performed on an image obtained from the inspection area under the condition of the second inspection mode.

Next, when an inspection is finished on entire region to be inspected in the wafer 115, an inspection result is output to the display system 101 (S514), and the processes of the image correction unit 113 are finished.

According to the present embodiment, since the defect is detected from the image captured by the image sensor 109 after correcting the image based on temperature measurement data of the image sensor 109 at the time of imaging, the inspection may be accurately performed even by using the image data obtained immediately after switching the inspection mode. As a result, immediately after switching the inspection mode, the inspection image may be generated without waiting for the stabilization of the temperature of the image sensor 109, and thus, the inspection throughput may be improved.

[MODIFIED EXAMPLE 2]

According to the method of the modified example 1, from the pattern information of the inspection area, a region to be inspected in the first inspection mode is extracted and the extracted region is inspected first in the first inspection mode, and then a region to be inspected in the second inspection mode is extracted and the extracted region is inspected in the second inspection mode.

On the other hand, according to the present modified example, a region to be inspected in the first inspection mode and a region to be inspected in the second inspection mode are discriminated from pattern information of the inspection area, the region to be inspected that is set in advance is identified by using location information of the wafer 115 while the stage control unit 106 moves the stage 108 continuously in one direction (X direction), and then, an inspection is performed by sequentially switching the inspection mode corresponding to the region to be inspected.

In the present modified example, the pattern information of the inspection area is obtained first, and then, the region to be inspected in the first inspection mode and the region to be inspected in the second inspection mode are discriminated (S601).

Next, the inspection area set with respect to each inspection mode is extracted by using location information of the wafer 115 while the stage control unit 106 moves the stage 108 continuously in one direction (X direction) (S602).

As a result, when the extracted region is the region to be inspected in the first inspection mode (e.g., high sensitivity observation mode), the device control system 120 controls each component of the inspection apparatus 100 to be set in a condition of the first inspection mode (S603), and in this state, the image sensor 109 captures an image of the wafer 115 and the inspection image generation unit 112 generates an inspection image (S604).

Next, the image processing system 111 obtains correction data from a first correction table corresponding to the first inspection mode retained in the memory 111, based on temperature information of the image sensor 109 detected by the temperature measurement unit 116 (S605).

Next, the inspection image generated by the inspection image generation unit 112 is corrected by the obtained correction data (S606).

The corrected inspection image is sent to the defect detection unit 118 and compared with a reference image to detect a defect (S607). The reference image may be generated by using the corrected inspection image or by using design data.

Processes from S604 to S607 are repeatedly performed on an image obtained from the inspection area under the condition of the first inspection mode.

Next, in a case in which the region extracted in step S602 for discriminating the region (S602) is a region to be inspected in the second inspection mode (e.g., high throughput mode), the device control system 120 controls each component in the inspection apparatus 100 to be set in a condition of the second inspection mode (S608), and in this state, the image sensor 109 captures an image of the extracted region of the wafer 115 and the inspection image generation unit 112 generates an inspection image (S609).

Next, the image processing system 111 obtains correction data from a second correction table corresponding to the second inspection mode stored in the memory 111, according to temperature information of the image sensor 109 detected by the temperature measurement unit 116 (S610).

Next, the inspection image generated by the inspection image Generation unit 112 is corrected by using the correction data obtained from the second correction table (S611).

The corrected inspection image is sent to the defect detection unit 118 and compared with a reference image to detect a defect (S612). The reference image may be Generated by using the corrected inspection image or by using design data.

Processes from S609 to S612 are repeatedly performed on an image obtained from the inspection area under the condition of the second inspection mode.

Next, it is checked whether the inspection on the entire region of the wafer 115 to be inspected is finished (S613), and when the inspection on the entire region to be inspected is finished (YES), an inspection result is output to the display system 101 (S614) and processes in the image correction unit 113 are terminated.

On the other hand, when it is determined that the inspection on the entire region to be inspected is not finished (NO) in step S412, the process returns to step S601 to continue the process.

According to the present embodiment, since the defect is detected from the image captured by the image sensor 109 after correcting the image based on temperature measurement data of the image sensor 109 at the time of imaging, the inspection may be accurately performed by using the image data obtained immediately after switching the inspection mode. As a result, immediately after switching the inspection mode, the inspection image maybe generated without waiting for the stabilization of the temperature of the image sensor 109, and thus, the inspection throughput may be improved in a case where the inspection is performed while switching the inspection mode.

Second Embodiment

FIG. 7 is a diagram illustrating a configuration of an inspection apparatus 700 according to a second embodiment of the present invention. In the first embodiment, the same reference numerals are used for the same elements as those of FIG. 1, and descriptions thereof are omitted.

Although the thermocouple measurement and the infrared ray measurement maybe used to measure the temperature of the image sensor 109 in the first embodiment, a difference between thermal conductivities and circuit latencies of the sensor and the temperature measurement unit may result in a time-lag between the measured temperature and an actual sensor temperature. In particular, when the inspection mode is the high throughput mode, image correction may not be performed with high accuracy.

The second embodiment is provided to address the above issue, and is provided with an image sensor 709 including light-shielding pixels that are not affected by the scattered light from the wafer 115. An output signal from the light-shielding pixel includes information on a dark-current that is relevant with a temperature of the image sensor 709.

In the present embodiment, a temperature calculation unit 701 that calculates a sensor temperature by using data of light-shielding pixels in a detected image is provided in the image processing system 711, a correction coefficient is selected from the correction coefficient table 300 retained in the memory 117 illustrated with reference to FIG. 1 based on the calculated sensor temperature and the image correction unit 113 performs image processes such as an offset process, a gain correction, etc. of an inspection image generated by the inspection image generation unit 112 by using the selected correction coefficient, and thus lightness discontinuity occurring immediately after switching the mode may be corrected.

FIG. 8 is a front view of an image sensor as an example of the image sensor 709 when the light-shielding pixel 710 is provided in the present embodiment. Also, FIG. 9 is a plan view of the image sensor 709. As the image sensor 709, a sensor in which photodetectina elements are arranged in a row (line sensor) is illustrated as an example, and light-shielding pixels 710 are provided at opposite sides of the image sensor 709 and effective pixels 701 for detecting the scattered light from the wafer 115 are provided between the light-shielding pixels 710.

A temperature of the effective pixel is derived by using a calculation such as linear interpolation, etc. from temperature measurement data obtained from an output (dark-current) of pixels (light-shielding pixels) 702 at opposite sides covered by the light-shielding pixels 710, and a correction coefficient is selected from an estimate value of the derived pixel temperature to correct the image.

The temperature measured from the output of the light-shielding pixel 702 reflects an actual temperature of the image sensor 709, and a time-lag caused according to the thermocouple measurement and the infrared ray measurement may be addressed. However, temperature profile of the effective pixels in the image sensor 709 may be complicated according to peripheral circuits, environmental temperature, etc., and there may be some cases in which the temperature may not be derived through an exact calculation.

FIG. 10 illustrates an example of an image sensor 7091 for addressing the above issue by providing a plurality of light-shielding pixels 711. In FIG. 10, the light-shielding pixels 711 are arranged with constant intervals therebetween, and a sensor temperature is calculated from a detection signal of each light-shielding pixel 711. Next, a correction coefficient according to the sensor temperature of each light-shielding pixel 711 is selected from the correction coefficient table, and a temperature of the effective pixel 701 between the light-shielding pixels 711 is estimated through a supplementing process and a calculation process.

Since the temperature profile of the image sensor 7091 may be more accurately estimated by arranging a plurality of light-shielding pixels, image correction may be performed with higher accuracy than that of the case, in which the light-shielding pixels 710 are provided only at the opposite sides as illustrated in FIGS. 8 and 9. However, an effective pixel area is reduced in order to increase a light-shielding pixel area.

Third Embodiment

FIG. 11 is a diagram illustrating a third embodiment of the present invention. In the third embodiment, a method of correcting lightness discontinuity in a case where an inspection mode of the detection system 114 is switched in an apparatus in which a plurality of light sources having different wavelengths (107 and 1107 in the example of FIG. 11) are loaded.

Since there is a wavelength of a laser beam that is easy to be scattered according to a width, a height, and a material of the pattern formed on the wafer 115, in an inspection apparatus 1100 including a plurality of light sources 107 and 1107 according to the present embodiment, the light sources 107 and 1107 may be selected according to the above condition Since an efficiency of converting photons to electrons (quantization efficiency) of the image sensor 109 varies depending on the wavelength, according to the present embodiment, by correcting the image including information about the light sources 107 and 1107, a corrected detection image may be obtained with high accuracy.

More specifically, in an image processing system 1111, a correction coefficient table for each temperature of the image sensor 109, for each pixel in the image sensor 109, for each inspection mode, and for each wavelength of the light sources 107 and 1107 is stored in the memory 1117, a correction coefficient is selected based on the temperature of the image sensor 109 measured by the temperature measurement unit 1116, and inspection mode information and light source information obtained from the mode information notification unit 103, and then a corrected inspection image may be obtained by correcting the image by using the inspection image and the correction coefficient.

According to the present embodiment, since the temperature profile of the sensor is changed because the quantization efficiency of the image sensor 109 varies depending on the wavelength of the light source, according to the present embodiment, the correction coefficient table is prepared for each wavelength of the light source and for each inspection mode, and thus the image correction of higher accuracy maybe performed and the idling period that is required to suppress the lightness discontinuity according to the prior art may be dependent, to thereby improve the throughput of the apparatus.

In the foregoing, the invention made by the inventor of the present invention has been concretely described based on the embodiment. However, it is needless to say that the present invention is not limited to the foregoing embodiment and various modifications and alterations can be made within the scope of the present invention. That is, the configuration (step) described in the above embodiment may be partially replaced by a step or unit having corresponding functions, or some of insubstantial functions may be omitted.

The invention claimed is:

1. An inspection apparatus comprising:
   a table unit that is movable with a sample placed thereon;
   a light irradiation unit irradiating the sample placed on the table unit with illuminating light;
   a detection optical system forming a scattered light image from the sample irradiated with the illumination light, and detecting the scattered light image by using an image sensor;
   an image processing unit receiving a signal from the image sensor of the detection optical system that detects the scattered light image to generate an image of the scattered light, and processing the generated image to detect a defect of the sample;
   an output unit outputting an image including the defect processed by the image processing unit; and
   a control unit controlling the table unit, the light irradiation unit, the detection optical system, and the image processing unit, wherein
   the image processing unit includes:
      an image generation unit receiving the signal from the image sensor to generate the image of the scattered light;
      an image correction unit correcting lightness discontinuity that occurs in the image of the scattered light, the image being generated by the image generation unit; and
      a defect detection unit detecting the defect of the sample by processing the image, the lightness discontinuity of which is corrected by the image correction unit,
   the control unit switches between a high sensitivity mode, in which a relatively narrow region of the sample is inspected with high sensitivity, and a high throughput mode, in which a relatively wide region of the sample is inspected at a relatively high speed, by controlling the table unit, the light irradiation unit, the detection optical system, and the image processing unit, and
   the image correction unit receives a signal detecting the scattered light image generated from the sample in a state in which the temperature of the image sensor is changing before being stabilized immediately after switching between the high sensitivity mode and the high throughput mode by the control unit and corrects lightness discontinuity occurring in the image of scattered light, the image being generated by the image generation unit.

2. The inspection apparatus of claim 1, wherein the detection optical system includes a temperature detection unit measuring the temperature of the image sensor, and the image correction unit calculates a correction coefficient of an output from the image sensor, according to a relationship between the temperature of the image sensor and a sensitivity of the image sensor stored in advance, based on temperature information of the image sensor detected by the temperature detection unit, and corrects the lightness discontinuity occurring in the image of the scattered light, the image being generated by the image generation unit, by using the correction coefficient.

3. The inspection apparatus of claim 1, wherein the image sensor of the detection optical system outputs a signal of a dark-current flowing in the image sensor with a signal of detecting the scattered light image from the sample, and the image correction unit calculates a correction coefficient of an output from the image sensor, from a relationship between the dark-current of the image sensor and the temperature of the image sensor stored in advance, according to the signal of the dark-current output from the image sensor, and corrects the lightness discontinuity occurring in the image of the scattered light, the image being generated by the image generation unit, by using the correction coefficient.

4. The inspection apparatus of claim 1, wherein correction coefficient data stored in the image correction unit in advance is data about the correction coefficient of the output from the image sensor, based on a relationship between the temperature of the image sensor and a sensitivity of the image sensor according to the high sensitivity mode and the high throughput mode switched by the control unit.

5. An inspection method comprising:
   irradiating a sample placed on a table unit from a light irradiation unit with illumination light from a light irradiation unit;
   generating a scattered light image by condensing the scattered light from the sample irradiated with the illumination light, in a detection optical system and detecting the generated scattered light image by using an image sensor;
   generating an image of the scattered light by receiving a signal from the image sensor that detects the scattered light image in an image processing unit and processing the generated image to detect a defect of the sample;
   outputting, by an output unit, an image including the defect processed by the image processing unit; and
   controlling, by a control unit, the table unit, the light irradiation unit, the detection optical system, and the image processing unit, wherein
   the detecting of the defect of the sample by the image processing unit includes:
   generating, by an image generation unit, an image of the scattered light after receiving a signal from the image sensor;
   correcting, by an image correction unit, a lightness discontinuity that occurs in the image of the scattered light, the image being generated by the image generation unit; and
   detecting, by a defect detection unit, a defect in the sample by processing the image, the lightness discontinuity of which is corrected by the image correction unit, the control unit switches between a high sensitivity mode, in which a relatively narrow region of the sample is inspected with high sensitivity and a high throughput mode, in which a relatively wide region of the sample is inspected at a relatively high speed, by controlling the table unit, the light irradiation unit, the detection optical system, and the image processing unit, and the image correction unit receives a signal detecting the scattered light image generated from the sample in a state in which the temperature of the image sensor is changing before being stabilized immediately after switching between the high sensitivity mode and the high throughput mode the control unit and corrects lightness discontinuity occurring in the image of scattered light, the image being generated by the image generation unit.

6. The inspection method of claim 5, wherein a temperature detection unit measures the temperature of the image sensor, and the image correction unit calculates a correction coefficient of an output from the image sensor, according to a relationship between the temperature of the image sensor and a sensitivity of the image sensor stored in advance, based on temperature information of the image sensor detected by the temperature detection unit, and corrects the lightness discontinuity occurring in the image of the scattered light, the image being generated by the image generation unit, by using the correction coefficient.

7. The inspection method of claim 5, wherein the image sensor outputs a signal of a dark-current flowing in the image sensor with a signal of detecting the scattered light image from the sample, and in the image correction unit, a correction coefficient of an output from the image sensor is calculated from a relationship between the dark-current of the image sensor and the temperature of the image sensor stored in advance, according to the signal of the dark-current output from the image sensor, and the lightness discontinuity occurring in the image of the scattered light, the image being generated by the image generation unit, is corrected by using the correction coefficient.

8. The inspection method of claim 5, wherein correction coefficient data stored in the image correction unit in advance is correction coefficient data of an output from the image sensor based on a relationship between a temperature of the image sensor and a sensitivity of the image sensor in correspondence with the high sensitivity mode and the high throughput mode switched by the control unit.

* * * * *